(12) United States Patent
Aebersold et al.

(10) Patent No.: US 8,231,538 B2
(45) Date of Patent: Jul. 31, 2012

(54) PERIVASCULAR PRESSURE SENSOR AND SENSING SYSTEM

(75) Inventors: Julia W. Aebersold, Floyds Knobs, IN (US); Guruprasad A. Giridharan, Louisville, KY (US); George M. Pantalos, Louisville, KY (US); Laman A. Gray, Jr., Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 311 days.

(21) Appl. No.: 12/070,554

(22) Filed: Feb. 19, 2008

(65) Prior Publication Data

US 2008/0208065 A1 Aug. 28, 2008

Related U.S. Application Data

(60) Provisional application No. 60/902,324, filed on Feb. 20, 2007.

(51) Int. Cl.
*A61B 5/02* (2006.01)
(52) U.S. Cl. ......... 600/485; 600/481; 600/486; 600/500
(58) Field of Classification Search .................. 600/485, 600/486, 488
See application file for complete search history.

(56) References Cited

U.S. PATENT DOCUMENTS

| | | | |
|---|---|---|---|
| 3,149,492 A | 9/1964 | Weinberg | |
| 4,256,094 A | 3/1981 | Kapp et al. | |
| 4,566,456 A * | 1/1986 | Koning et al. | 607/23 |
| 4,669,485 A | 6/1987 | Russell | |
| 4,718,426 A | 1/1988 | Russell | |
| 4,718,427 A | 1/1988 | Russell | |

(Continued)

FOREIGN PATENT DOCUMENTS

WO WO 02-076289 10/2002

OTHER PUBLICATIONS

Chatzandroulis, S. et. al., "A miniature pressure system with a capacitive sensor and a passive telemetry link for use in implantable applications", *Journal of Microelectromechanical Systems*, vol. 9, Issue 1, Mar. 2000.

(Continued)

*Primary Examiner* — Charles A Marmor, II
*Assistant Examiner* — Michael D'Angelo
(74) *Attorney, Agent, or Firm* — Greer, Burns & Crain Ltd.

(57) ABSTRACT

An embodiment of the invention is an in-vivo blood pressure sensor device including a strain transducer and flexible biocompatible material that carries the strain transducer. The flexible biocompatible material is configured to encircle the outside of a blood vessel when surgically installed. A preferred embodiment in-vivo blood pressure sensor device of the invention includes a strain transducer carried by a flexible biocompatible ring that is configured to be surgically installed to encircle a blood vessel. The device also includes passive circuitry encased in biocompatible material for sensing strain in the strain transducer and for providing data to an external reader. The passive circuitry is also configured to be surgically installed in a subject. The device further includes a telemetry coil encased in biocompatible material and configured to be surgically installed in a subject, to receive power via inductive coupling to an external reader, to supply power to the passive circuitry and to act as an antenna for communications with an external reader.

14 Claims, 7 Drawing Sheets

U.S. PATENT DOCUMENTS

| | | | |
|---|---|---|---|
| 4,718,428 | A | 1/1988 | Russell |
| 4,881,939 | A | 11/1989 | Newman |
| 4,926,875 | A | 5/1990 | Rabinovitz et al. |
| 6,106,477 | A | 8/2000 | Miesel et al. |
| 6,208,902 | B1 * | 3/2001 | Boveja .............................. 607/46 |
| 6,442,413 | B1 * | 8/2002 | Silver .............................. 600/345 |
| 6,471,656 | B1 | 10/2002 | Shalman et al. |
| 7,017,420 | B2 | 3/2006 | Kalvesten et al. |
| 7,048,691 | B2 | 5/2006 | Miele et al. |
| 7,118,534 | B2 | 10/2006 | Ward et al. |
| 2004/0133092 | A1 * | 7/2004 | Kain .............................. 600/377 |
| 2006/0084835 | A1 * | 4/2006 | Laufer .............................. 600/16 |
| 2006/0122522 | A1 * | 6/2006 | Chavan et al. ................ 600/505 |
| 2006/0137457 | A1 * | 6/2006 | Zdeblick ......................... 73/715 |

OTHER PUBLICATIONS

Hierold, C., et. al "Implantable low power integrated pressure sensor system for minimal invasive telemetric patient monitoring", *Micro Electra Mechanical Systems, 1998. MEMS 98. Proceedings., The Eleventh Annual International Workshop* on, Jan. 25-29, 1998.

Kalvesten, E., et. al. "The first surface micromachined pressure sensor for cardiovascular pressure measurements", *Micro Electra Mechanical Systems, 1998. MEMS 98. Proceedings., The Eleventh Annual international Workshop* on, Jan. 25-29, 1998.

* cited by examiner

PERIVASCULAR PRESSURE SENSOR AND SENSING SYSTEM

PRIORITY CLAIM AND REFERENCE TO RELATED APPLICATION

The application claims priority under 35 U.S.C. §119 from prior provisional application Ser. No. 60/902,324, which was filed on Feb. 20, 2007.

FIELD

A field of the invention is medical devices. The invention concerns a blood pressure sensing device and system.

BACKGROUND

Blood pressure is one of the key hemodynamic parameters that are measured. Direct measurement of blood pressure in blood vessels provides accuracy that is valuable in many instances, such as during surgical procedures. Direct measurement of blood pressure in blood vessels, however, is limited by current technology.

For surgical patients, a need can be present to measure pressure over an extended duration, exceeding several days. Extended measurements are limited by current technology, for they involve direct contact with the blood stream, where concerns arise with the risk of thrombus formation and septicemia. In addition to the risks presented to the patient, a direct blood contact sensor tends to become less accurate over time due to signal drift and the formation of a biolayer, which reduces sensitivity and defeats the purpose of direct in-vivo blood pressure measurements.

Millar Instruments makes in-vivo blood contact sensors (Millar Mikro-Tip® pressure catheters) that are widely used in clinical studies. The Millar Instruments' device includes a piezoresistive pressure sensor encased in a catheter tip, which is inserted into the blood vessel. Millar Instruments' PVR-1045 and SPR-1000 devices have ultra-miniature catheters that are intended for use in small animal research. The catheter tip size of ⅓ mm minimizes blood flow obstruction in the vessel being monitored. However, the catheter style device still raises a risk of thrombus formation and septicemia in human patients.

Deltran also makes a disposable pressure sensor for in-vivo use. U.S. Pat. No. 6,117,086 discloses a Deltran sensor, which includes a semiconductor strain gage connected to a fluid-filled catheter/manometer system. The catheter is coupled with a strain gage through a disposable dome having a compliant isolation media that contacts the strain gage. The dome is configured to provide an electrical and biological barrier between the fluid in communication with the invasive catheter and the strain gage's diaphragm. However, this approach does not minimize the complications stated above because the primary transduction method requires an invasive catheter. Other companies, e.g., Integra™, also make similar devices. The Camino® line of intracranial pressure sensors of Integra™ is another example of the catheter approach for in-vivo pressure measurement.

Improving pressure sensing monitoring remains an issue of interest in part due to the limitations of current commercially available devices. Examples of the research are in the following publications. Kalvesten, et al, "The First Surface Micromachined Pressure Sensor for Cardiovascular Pressure Measurements," Micro Electro Mechanical Systems Proceedings, The Eleventh Annual International Workshop, p. 574-579, (Jan. 25-29 1998), discloses a device that uses a catheter, which risks thrombosis formation or septicemia. Chatzandroulis, S.; et al, "A Miniature Pressure System with a Capacitive Sensor and a Passive Telemetry Link for Use in Implantable Applications," Journal of Micro Electro Mechanical Systems, vol. 9, no. 1 pp. 18-23, (March 2000) describes a device that uses a capacitive pressure sensor to be packaged within a catheter. The catheter approach, again, risks thrombosis formation or septicemia. Similar efforts are described in Hierold, C.; et al "Implantable Low Power Integrated Pressure Sensor System for Minimal Invasive Telemetric Patient Monitoring," Micro Electro Mechanical Systems Proceedings, The Eleventh Annual International Workshop, pp. 574-579, (Jan. 25-29 1998), and in U.S. Pat. Nos. 4,718,426; 4,718,427; 4,718,428; 4,669,485; 6,471,656; 7,118,534; 7,048,691; and 7,017,420.

SUMMARY OF THE INVENTION

An embodiment of the invention is an in-vivo blood pressure sensor device including a strain transducer and flexible biocompatible material that carries the strain transducer. The flexible biocompatible material is configured to encircle the outside of a blood vessel when surgically installed. A preferred embodiment in-vivo blood pressure sensor device of the invention includes a strain transducer carried by a flexible biocompatible ring that is configured to be surgically installed to encircle a blood vessel. The device also includes passive circuitry encased in biocompatible material for sensing strain in the strain transducer and for providing data to an external reader. The passive circuitry is also configured to be surgically installed in a subject. The device further includes a telemetry coil encased in biocompatible material and configured to be surgically installed in a subject, to receive power via inductive coupling to an external reader, to supply power to the passive circuitry and to act as an antenna for communications with an external reader.

DETAILED DESCRIPTION OF THE PREFERRED EMBODIMENTS

Figure 1:
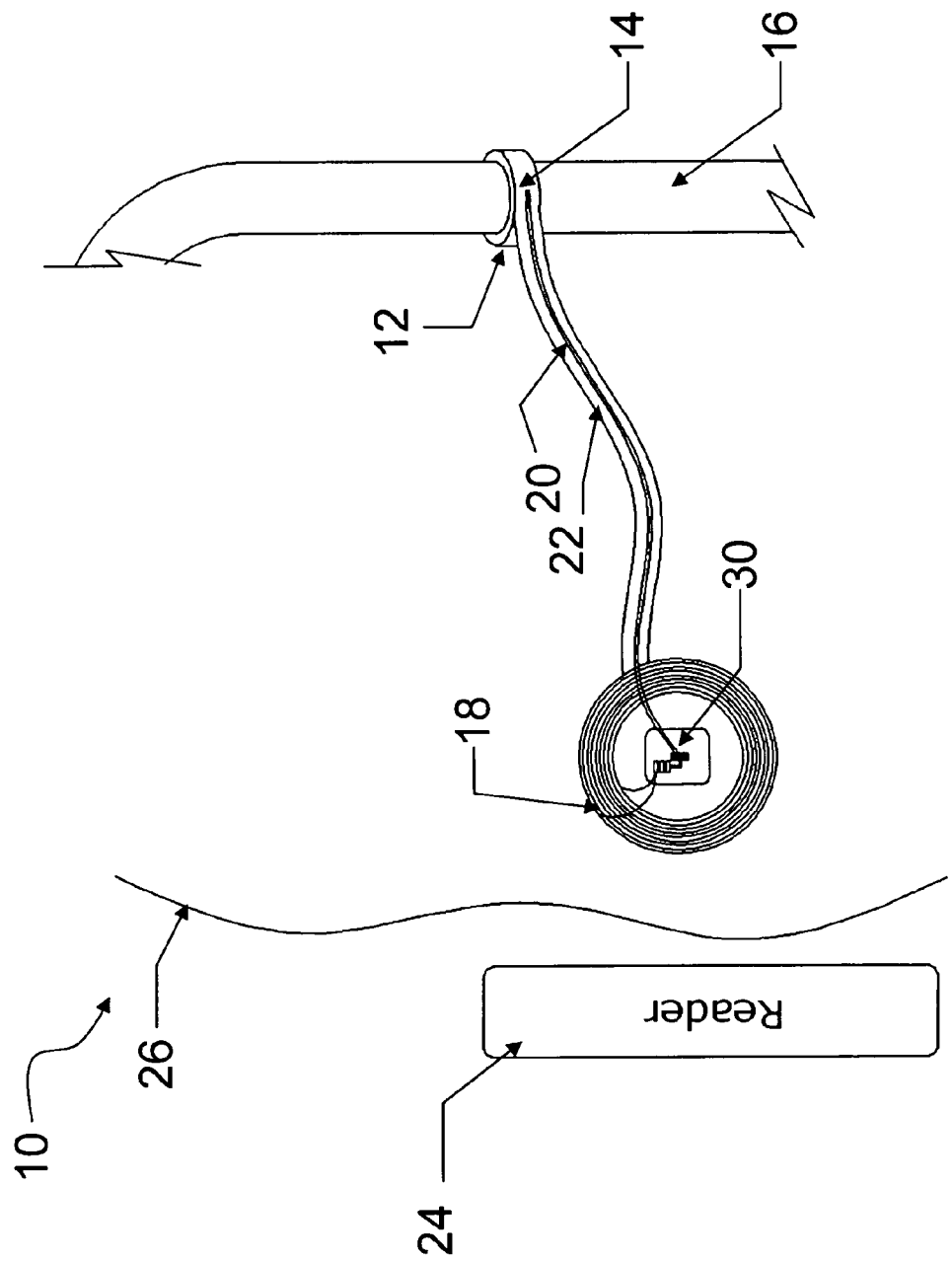
FIG. 1 is a schematic illustration of a preferred embodiment perivascular pressure monitoring system of the invention.

The invention provides an in-vivo pressure sensor paired with a passive telemetry system that detects pressure and avoids risks associated with catheter based systems. A monitoring device of the invention does not penetrate the blood vessel being monitored, and thereby avoids risks associated with thrombus formation and septicemia. Devices of the invention minimize risks presented to a patient, and are also suited for long term testing and trend data. No direct blood contact sensor is used, and devices of the invention therefore avoid signal drift and biolayer formation that arise from such direct blood contact. A preferred embodiment device is an in-vivo perivascular blood pressure sensor that includes a strain transducer. The strain transducer is encased in a flexible biocompatible material that is configured to encircle the outside of a blood vessel. In preferred embodiments, a sensor device also includes an implantable coil to permit a reader to communicate with the transducer and supply power for obtaining readings via an inductive coupling. A preferred embodiment sensing system of the invention includes an in-vivo perivascular blood pressure sensor and a reader that inductively couples to, supplies power to, and takes readings from a sensor device of the invention.

A preferred embodiment of the invention is an in-vivo perivascular pressure sensor device that includes a strain transducer encased in a flexible biocompatible material configured to attach to the outside perimeter of a blood vessel. The preferred device also includes a passive telemetry coil that enables a reader to inductively couple to the coil, send power to the passive circuitry, and take readings from the strain transducer. In one embodiment, the coil is configured to be implanted just below the skin and connect via lead wires to the sensor. In other embodiments, the passive telemetry coil is configured to be placed adjacent to the pressure sensor or is contained within the flexible biocompatible material that is configured to encircle the blood vessel. Preferred embodiment sensor devices can also provide flow sensing.

A preferred embodiment of the invention includes a piezoresistive transducer or a plurality thereof arranged in an electrical circuit and encased in a flexible biocompatible material configured to attach to the outside perimeter of a blood vessel. In preferred embodiments, the piezoresistive transducer is a silicon piezoresistive transducer. In a preferred embodiment, the transducer is encapsulated in a biocompatible material, e.g., silicone, forming an open ring, and is surgically installed with a closing mechanism around the blood vessel, e.g., suture, tie, stitch, adhesive or other joining of the ring such that it is fixed around the blood vessel.

Implantation of the sensor and system components of the invention will occur during surgery. In a preferred embodiment, the transducer is a silicon piezoresistor or plurality thereof. Readings from the transducer, which does not require an active power source, can be acquired through inductive coupling to the transducer. A preferred system includes a remote in-vivo compatible coil to act as an antenna, which communicates with an external reader to obtain readings from the transducer.

Preferred embodiment devices of the invention can detect pressure changes existing in the blood vessel and generate pressure data that can be used for profile and trend data. Preferred embodiment devices can be implanted for a prolonged period (chronic/permanent implantation) without contact to the blood stream, thus reducing the risk of potential complications.

Preferred embodiment sensor systems of the invention transmit data wirelessly via RFID technology to avoid infection of subcutaneous tissue. In preferred embodiments, an active in-vivo power source is not required, thus enabling long term implantation without associated concerns of battery degradation, charge duration and recharging.

Preferred embodiment sensors of the invention are formed using a biocompatible material. Such embodiments of the invention can be retrieved by minimally invasive surgical techniques, if needed.

Preferred embodiments provide power to the system and obtain readings via radio frequency telemetry. Other embodiments can provide power and obtain readings through wires.

Preferred embodiment sensors and sensor systems of the invention will now be discussed with respect to the drawings. The drawings include schematic figures, which will be understood by artisans with reference to the description below. The drawings are not to scale and features in the drawings may be exaggerated for purposes of illustration.

Figure 2:
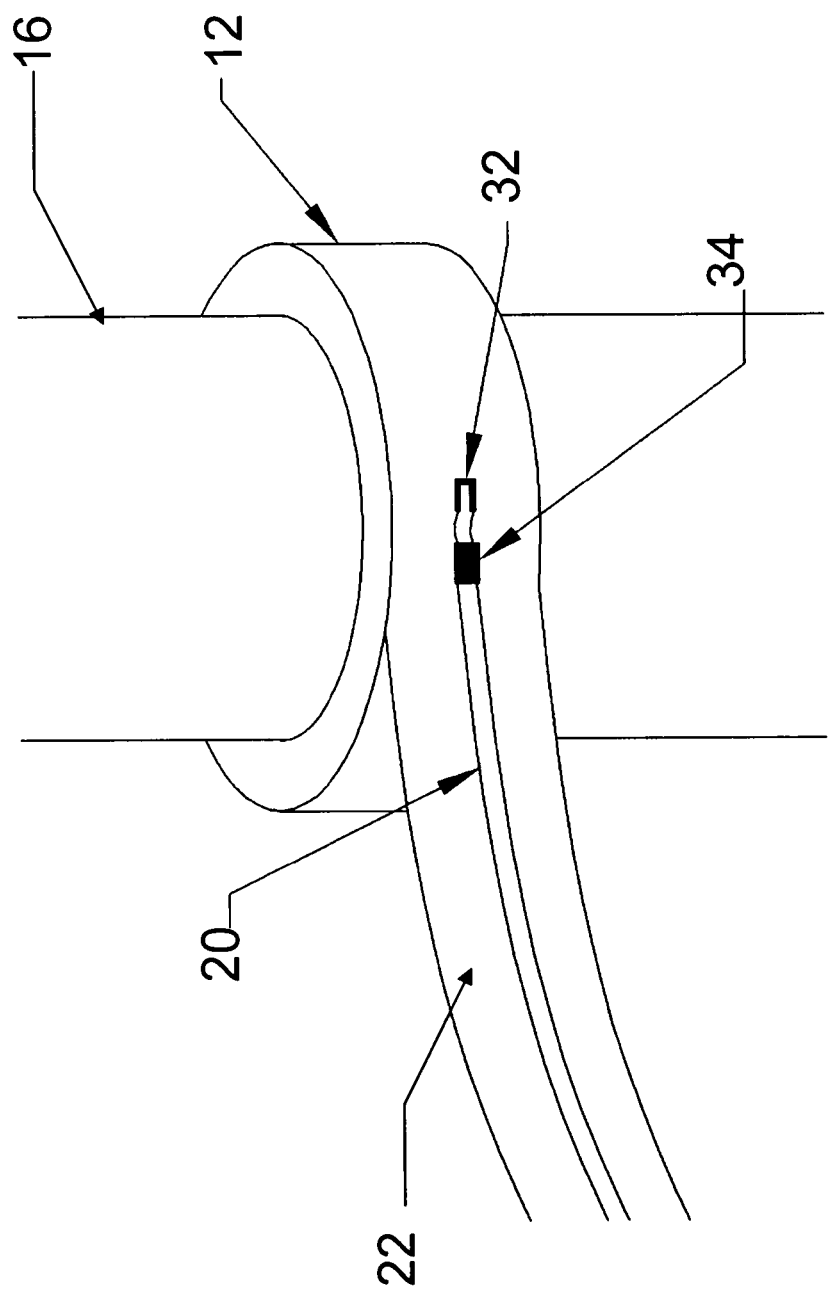
FIG. 2 illustrates a transducer portion of the system of FIG. 1.
Figure 3:
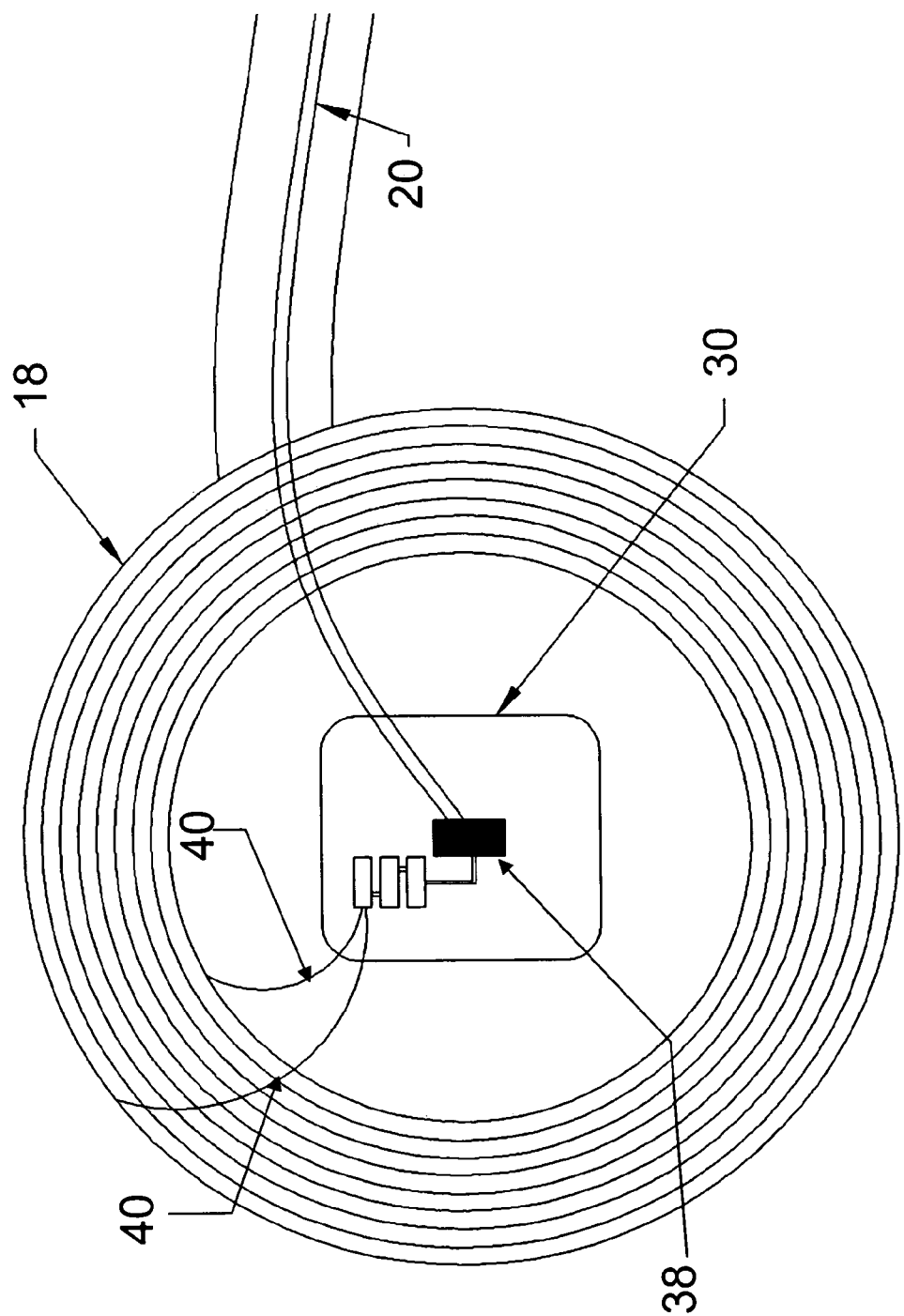
FIG. 3 illustrates a telemetry antenna portion of the system of FIG. 1.

FIGS. 1-3 illustrate a preferred embodiment perivascular blood pressure monitoring system 10. The system has a flexible biocompatible (e.g. silicone) ring 12 that carries, and may encase, a strain transducer 14 placed around a blood vessel 16. The strain transducer can be a polysilicon piezoresistor. A remote passive telemetry coil 18 connects via leads 20 to the strain transducer 14. The leads are encased in biocompatible sheath 22, formed preferably from the same unitary material as a continuous part of the ring 12. Power is supplied via inductive coupling from an external reader 24 via the telemetry coil 18, which also acts as an antenna to transmit data to the reader 24. The coil 18 is shown in FIG. 1 as implanted just under the skin 26 of a subject. The sheath 22 and the leads 20 have a length to permit the coil 18 to be extended away from the blood vessel 16 and the ring 12 so that the coil 18 can be installed near the skin 26. The coil surrounds an RFID telemetry circuit 30, which is similarly protected by a biocompatible material such as silicone. The external reader 24 powers the RFID telemetry circuit and receives strain information obtained by the circuit 30 from the strain transducer 14 via the leads 20. During surgery, the silicone ring 12 with the strain transducer 14 are placed around the blood vessel 16, and the RFID telemetry circuit 30 and inductive power coil 18 are placed just beneath the skin 26.

FIG. 2 illustrates the strain transducer, which preferably includes a silicon piezoresistor 32 or an arrangement of silicon piezoresistors and an application specific integrated circuit (ASIC) 34 that receives power through the leads 20 and communicates with the RFID telemetry circuit 30 through the leads. The ring 12 undergoes a deformation during each pressure pulse in the vessel 16 causing a change in output resistance from the silicon piezoresistor 32, where resistance values can be correlated to pressure. Trend data can also be gathered over a period of time, offering more useful information about large variations in absolute pressure amongst patients.

FIG. 3 illustrates the telemetry portion of the pressure sensing system 10. The remote coil 18 is encased in biocompatible material, e.g., silicone, and houses the telemetry circuit 30 including an ASIC 38 that attaches to the coil 18 via leads 40 in the silicone ring and serves as an antenna for the system. The primary purpose of the coil 18 is to receive power for the circuits 34 and 38 and components via inductive coupling from the external reader. Additionally, the implanted coil 18 serves as an antenna for transmitting data to the external reader 24. As the reader 24 is external, it can be of a relatively large size and meet system power requirements. Additionally, the reader can communicate with other devices, such as a wireless or wired network to collect data from one or more subjects monitoring pressure with a pressure sensor device of the invention implanted in the subject.

Figure 4:
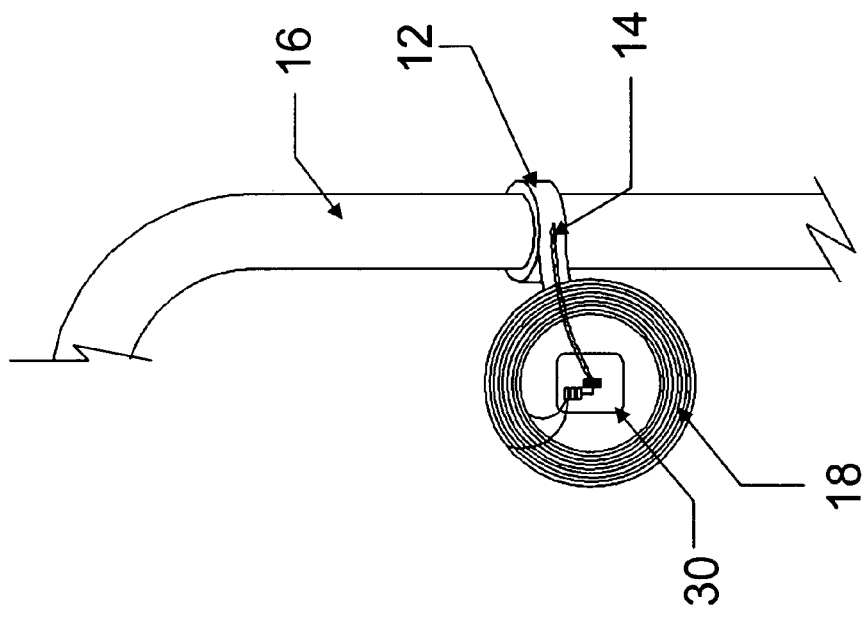
FIG. 4 is a schematic illustration of another preferred embodiment perivascular pressure monitoring system of the invention.
Figure 4:
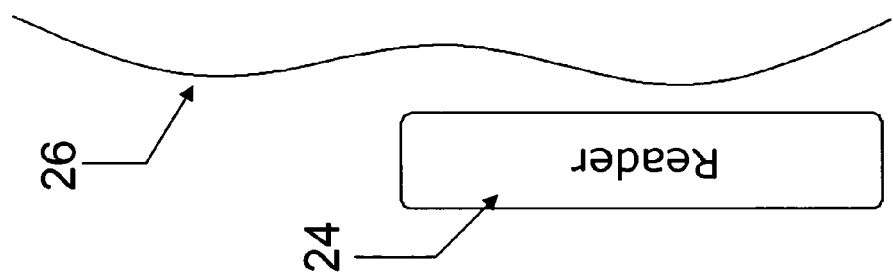
Figure 5:
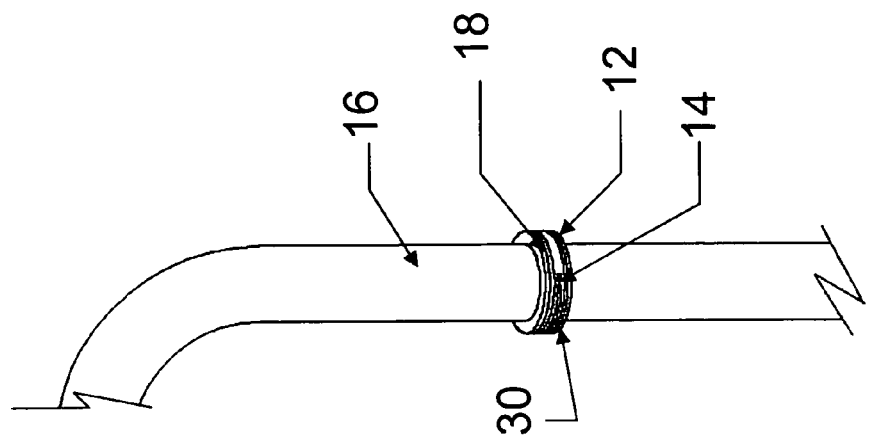
FIG. 5 is a schematic illustration of another preferred embodiment perivascular pressure monitoring system of the invention.
Figure 5:
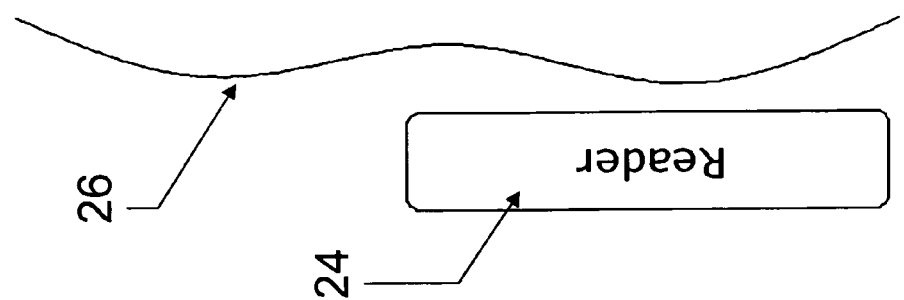

Additional embodiment pressure sensor systems of the invention are shown in FIGS. 4 and 5. In FIGS. 4 and 5, comparable parts of the systems are labeled with the part numbers used in FIGS. 1-3. In FIG. 4, the leads 20 and their casing are very short so that the coil 18 and the telemetry circuit 30 are necessarily caused to be adjacent to the vessel 16 that is being monitored. The coil 18 and telemetry circuit 30 are adjacent the strain transducer 14. In FIG. 5, the coil 18 and telemetry circuit 30 are within the ring 12, which can be made large enough to accommodate the coil 18 and telemetry circuit 30. The FIGS. 4 and 5 embodiments provide for an easier surgical installation of the pressure monitoring system, but will have a reduced signal to noise ratio compared to the FIGS. 1-3 embodiment where the coil is located near the skin 26.

Figure 6:
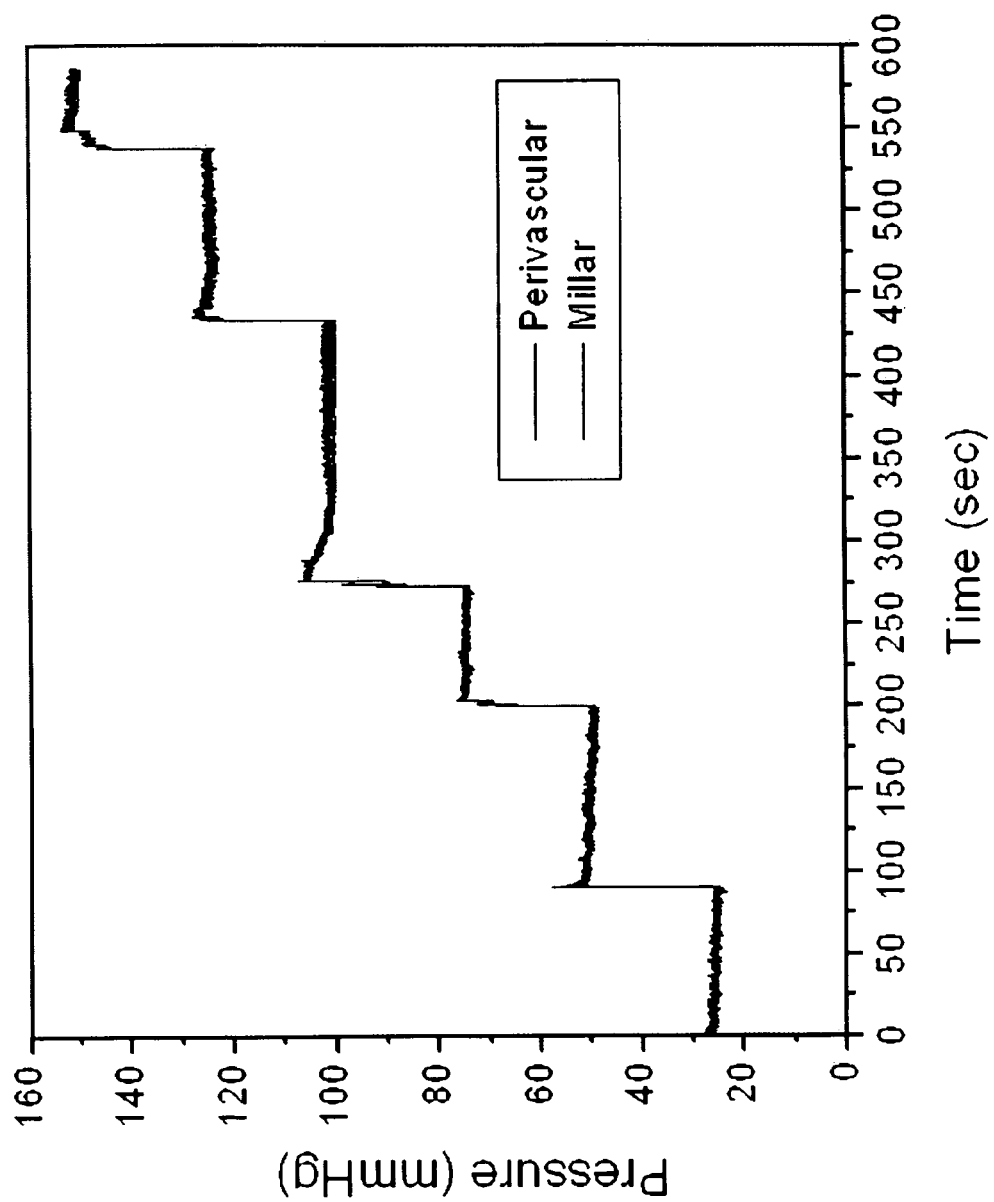
FIG. 6 plots test data comparing an experimental device of the invention to a commercial device that uses a catheter sensor over a number of static pressures on a mock circulatory system.
Figure 7:
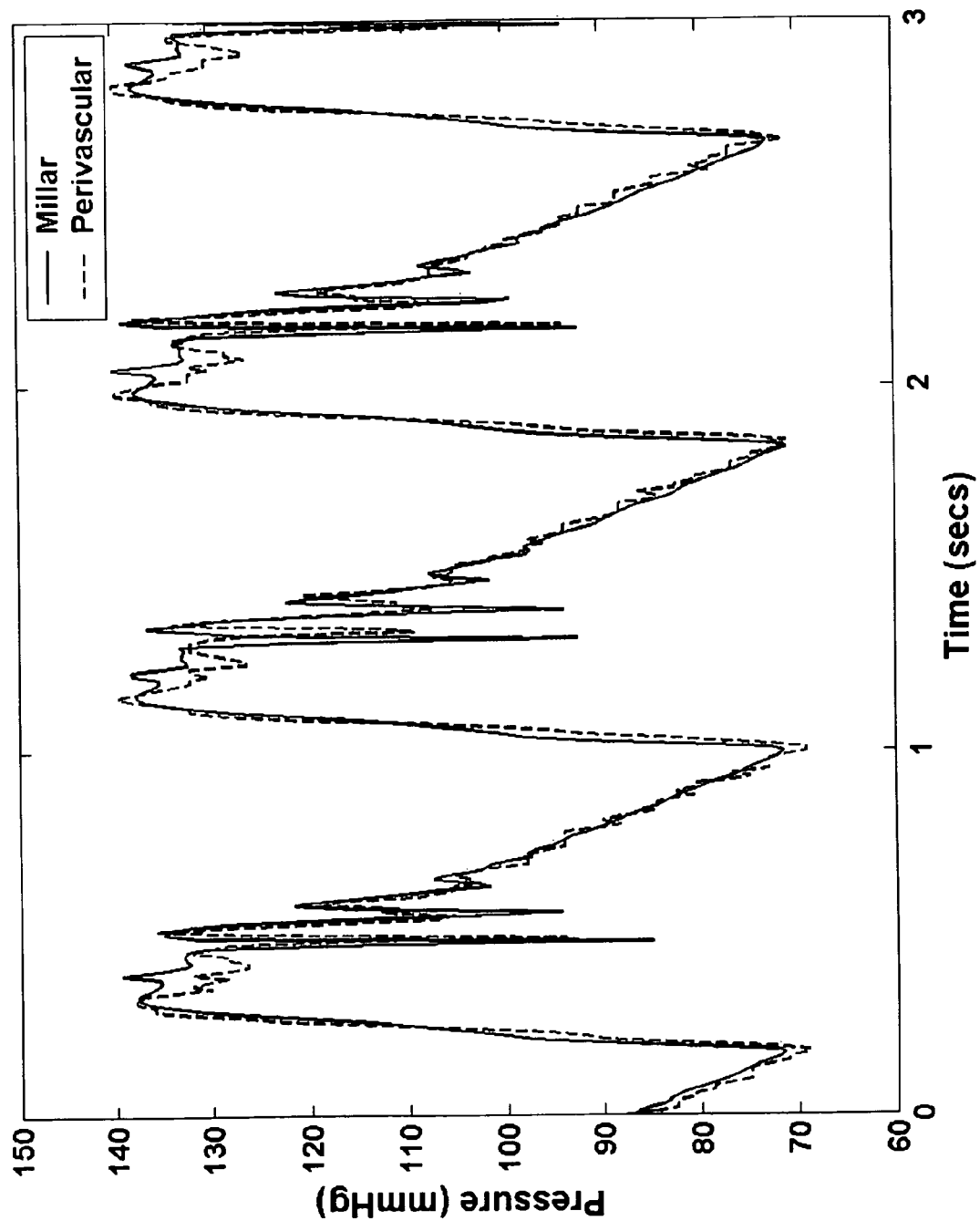
FIG. 7 plots test data comparing an experimental device of the invention to a commercial device that uses a catheter sensor over a simulated human systolic and diastolic dynamic range on a mock circulatory system.

FIGS. 6 and 7 are data collected from an experimental perivascular pressure sensor system of the invention and a commercial Millar catheter tip pressure sensing system. The data were collected from a mock circulatory system from static pressure conditions (FIG. 6) and dynamic data (FIG. 7). The mock circulatory system was an adult mock circulation system consisting of a mock left ventricle, and systemic vasculature with a compliant mock aorta, and was used to test the efficacy, fidelity and sensitivity of the prototype sensor system. The drive line pressure for the ventricular sac and mock vascular resistance were adjusted to produce pressures and flows reported clinically for normal and hypertensive humans. The mock circulation system is similar to those previously used in tests. See, e.g., Pantalos GM, et al. "Characterization of an Adult Mock Circulation for Testing Cardiac Support Devices." ASAIO Journal. 50(1):37-46, January/February 2004. The dynamic data was consistent with a pressure range for systolic and diastolic pressures in a human. These data show good correlation between the two systems. Thus, a device and system of the invention produces results commensurate with commercially available devices, while avoiding the risks and drawbacks associated with catheter tip mounted pressure transducers.

As will be appreciated by artisans from the preferred embodiments, sensor devices and sensor systems of the invention provide for high fidelity pressure monitoring in-vivo. An external reader can provide information to a controller or control other devices based upon readings from the sensor system, e.g., cardiac assist devices (ventricular assist devices, myocardial recovery devices, total artificial hearts etc.).

Artisans will appreciate many important uses for sensor devices and sensor systems of the invention. Sensor devices and sensor systems of the invention can detect blockage in blood vessels. For example, a bypass coronary artery blockage causes a drop in pressure, which can be measured using a sensor system of the invention. This eliminates the need for frequent monitoring via imaging techniques. Sensors of the invention can also provide feedback control for pacemaker firing rates (measure pressure in the carotid artery and fire the pacemaker to meet physiologic demand). Sensors and sensor systems of the invention can be used in clinical studies, for acute and chronic pressure monitoring in laboratory animals.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. An in-vivo blood pressure sensor system, comprising:
a strain transducer;
flexible biocompatible material that carries said strain transducer, wherein said flexible biocompatible material comprises a ring configured to encircle the outside of a blood vessel when surgically installed by a closing mechanism
a telemetry coil;
an RFID telemetry circuit;
a passive strain sensing circuit to determine strain in said strain transducer;
leads permitting data and power transfer between said RFID telemetry circuit and said strain sensing circuit; and
additional flexible biocompatible material encasing said coil, said telemetry circuit, said strain sensing circuit and said leads.

2. The sensor system of claim 1, wherein said flexible biocompatible material further comprises a sheath encasing said leads.

3. The sensor system of claim 2, wherein said sheath and said leads have a length to permit the coil to be extended away from the ring a distance allowing the coil to be installed near the skin of a subject.

4. The sensor system of claim 2, wherein said sheath and said leads have a length to cause the coil to be adjacent the ring when the ring is installed on the blood vessel.

5. The sensor system of claim 1, wherein said ring and is configured to encase said coil, said telemetry circuit, said strain sensing circuit and said leads.

6. The sensor system of claim 1, wherein said strain transducer comprises a silicon piezoresistor.

7. The sensor system of claim 1, wherein said biocompatible material comprises silicone.

8. A system for in-vivo blood pressure measurement, the system comprising:
the system of claim 1, and
an external reader for inductively coupling to said sensor device via the telemetry coil to supply power to said sensor device and receive data from said RFID telemetry circuit.

9. An in-vivo blood pressure sensor device, comprising:
a strain transducer carried by a flexible biocompatible ring that is configured to be surgically installed to encircle a blood vessel;
passive circuitry encased in biocompatible material for sensing strain in said strain transducer and for providing data to an external reader, said passive circuitry being configured to be surgically installed in a subject; and
a telemetry coil encased in biocompatible material and configured to be surgically installed in a subject, to receive power via inductive coupling to an external reader, to supply power to said passive circuitry and to act as an antenna for communications with an external reader.

10. The sensor device of claim 9, wherein said flexible biocompatible ring and the biocompatible material encasing said passive circuitry and said telemetry coil is the same unitary material of the flexible biocompatible ring.

11. The sensor device of claim 10, wherein said flexible biocompatible material is silicone.

12. The sensor device of claim 11, wherein said strain transducer comprises a silicon piezoresistor.

13. A system for in-vivo blood pressure measurement, the system comprising:
a sensor device of claim 9, and
an external reader for inductively coupling to said sensor device via the telemetry coil to supply power to said passive circuitry and receive data from said passive circuitry.

14. An in-vivo blood pressure sensor device, comprising:
a strain transducer carried by a flexible biocompatible ring that is configured to be surgically installed to encircle a blood vessel;
biocompatible passive circuitry means for sensing strain in said strain transducer and providing data to an external reader; and
biocompatible RFID means for receiving power from and communicating data to an external reader.

* * * * *

UNITED STATES PATENT AND TRADEMARK OFFICE
CERTIFICATE OF CORRECTION

PATENT NO. : 8,231,538 B2
APPLICATION NO. : 12/070554
DATED : July 31, 2012
INVENTOR(S) : Julie W. Aebersold et al.

It is certified that error appears in the above-identified patent and that said Letters Patent is hereby corrected as shown below:

In the Claims:

Col. 6, line 16    Please delete "and" after "said ring".

Signed and Sealed this
Twenty-sixth Day of February, 2013

Teresa Stanek Rea
*Acting Director of the United States Patent and Trademark Office*